United States Patent
Furuya et al.

(10) Patent No.: US 6,770,796 B2
(45) Date of Patent: Aug. 3, 2004

(54) ABSORBENT ARTICLE WITH SURFACE MEMBER OF CONTINUOUS FILAMENTS

(75) Inventors: Kodai Furuya, Kagawa (JP); Hiroo Hayashi, Kagawa (JP); Takamitsu Igaue, Kagawa (JP)

(73) Assignee: Uni-Charm Corporation, Kawanoe (JP)

( * ) Notice: Subject to any disclaimer, the term of this patent is extended or adjusted under 35 U.S.C. 154(b) by 239 days.

(21) Appl. No.: 10/004,754

(22) Filed: Dec. 3, 2001

(65) Prior Publication Data

US 2002/0072724 A1 Jun. 13, 2002

(30) Foreign Application Priority Data

Dec. 12, 2000 (JP) ........................................ 2000-377018

(51) Int. Cl.[7] .............................................. A61F 13/15
(52) U.S. Cl. ................. 604/384; 604/378; 604/385.101
(58) Field of Search ............................ 604/385.01, 384, 604/378, 372, 365, 366, 377, 385.101; 442/366, 369, 374, 381, 403

(56) References Cited

U.S. PATENT DOCUMENTS

| | | | | |
|---|---|---|---|---|
| 3,727,615 A | * | 4/1973 | Duchane | 604/365 |
| 4,360,022 A | * | 11/1982 | Usami et al. | 604/368 |
| 4,676,786 A | * | 6/1987 | Nishino | 604/378 |
| 4,685,914 A | * | 8/1987 | Holtman | 604/368 |
| 4,910,064 A | * | 3/1990 | Sabee | 428/113 |
| 5,342,336 A | * | 8/1994 | Meirowitz et al. | 604/378 |
| 5,669,895 A | * | 9/1997 | Murakami et al. | 604/380 |
| 5,925,581 A | * | 7/1999 | Tolbert | 442/334 |
| 6,417,427 B1 | * | 7/2002 | Roxendal et al. | 604/378 |

* cited by examiner

Primary Examiner—John J. Calvert
Assistant Examiner—Jacqueline F Stephens
(74) Attorney, Agent, or Firm—Darby & Darby

(57) ABSTRACT

Disclosed is an absorbent article including a liquid-permeable surface member, a backsheet and an absorbent core positioned between the surface member and the backsheet. The surface member is a sheet including: first continuous filaments made of hydrophobic synthetic resin and individually extending over the entire length of the surface member; and second continuous filaments made of cellulose acetate and individually extending over the entire length of the surface member.

7 Claims, 4 Drawing Sheets

ABSORBENT ARTICLE WITH SURFACE MEMBER OF CONTINUOUS FILAMENTS

BACKGROUND OF THE INVENTION

1. Field of the Invention

The present invention relates to an absorbent article such as sanitary napkin, disposable diaper, incontinence pad, or the like, which is provided with a surface member excellent in moisture-absorbency and liquid-permeability.

2. Description of the Related Art

Absorbent articles such as sanitary napkin, disposable diaper, or the like are typically constructed to include: a liquid-impermeable backsheet on its garment-facing side, a liquid-permeable surface member on its wearer-facing side, and an absorbent core disposed between the backsheet and the surface member.

Characteristics required for the surface member of the absorbent article are as follows:

1) The surface member is excellent in liquid-permeability so as to introduce liquid into the absorbent core;
2) Liquid once absorbed by the absorbent core hardly leaks back through the surface member (i.e., the phenomenon called "rewet back" hardly occurs); and
3) The surface member is excellent in moisture-absorbency so as not to provide unpleasant, stuffy feel to a wearer.

For example, Japanese Unexamined Patent Publication Nos. 1998-219568 and 1994-218007 disclose absorbent articles having surface members in which both liquid-permeability and moisture-absorbency are improved.

In Japanese Unexamined Patent Publication No. 1998-219568, water-absorbency or moisture-absorbency is improved by adhering hydrophilic powder to the surface of a nonwoven fabric treated to be water repellent.

In Japanese Unexamined Patent Publication No. 1994-218007, on the other hand, moisture-absorbency is improved by fixing a moisture-absorbent material to an absorbent article or by mixing a moisture-absorbent material in a surface member.

However, the hydrophilic powder disclosed in Japanese Unexamined Patent Publication No. 1998-219568 is apt to drop off from the surface of the nonwoven fabric, so that there is a difficulty in maintaining absorbency. In addition, since powder material and powder coating are required, production cost becomes relatively expensive.

On the other hand, the moisture-absorbent material disclosed in Japanese Unexamined Patent Publication No. 1994-218007, which is aimed solely at absorbing moisture, has difficulties in fixing it inside of the absorbent article. In addition, the absorbent article is liable to give wet feel to the wearer's skin as a whole. This is because moisture-absorbing capacity is decreased in the surface member as located farther from the moisture-absorbent material, although moisture-absorbency is improved in the vicinity of the moisture-absorbent material. In case where the moisture-absorbent material is mixed in the surface member, on the other hand, fixing of the moisture-absorbent material is typically carried out by hydroentangling method. Therefore, a hydrophilic agent applied to the synthetic resin flows out due to water flow, thereby lowering the water-absorbing capacity.

SUMMARY OF THE INVENTION

The present invention has been worked out in view of the shortcoming in the prior art set forth above. It is therefore an object of the present invention to provide an absorbent article with a surface member excellent in both liquid-permeability and moisture-absorbency.

According to the present invention, there is provided an absorbent article comprising a liquid-permeable surface member, a backsheet and an absorbent core positioned between the surface member and the backsheet, the surface member being a sheet comprising: first continuous filaments made of hydrophobic synthetic resin and individually extending over the entire length of the surface member; and second continuous filaments made of cellulose acetate and individually extending over the entire length of the surface member.

In the absorbent article of the present invention, the first continuous filaments of hydrophobic synthetic resin allow a liquid to pass through the surface member and also exhibit a function to prevent flow back of the liquid from the absorbent core to the surface of the surface member. On the other hand, the second continuous filaments of cellulose acetate can effectively absorb moisture. Therefore, the surface of the absorbent article is always kept dry, and hardly gives stuffy feel to a wearer. In addition, the surface member has excellent cushioning properties because it is formed from the continuous filaments, providing softness when in contact with the wearer's skin. Accordingly, the absorbent article of the present invention prevents skin roughness of a wearer.

Preferably, the first continuous filaments are treated to be hydrophilic, and hydrophilicity of the second continuous filaments is higher than hydrophilicity of the first continuous filaments.

For example, the surface member comprises: first portions formed from the first continuous filaments; and second portions formed from the second continuous filaments, the first portions alternating with the second portions. Alternatively, the first continuous filaments and the second continuous filaments are mixed with each other in the surface member.

The surface member may further comprise a liquid-permeable substrate sheet underlying the first and second continuous filaments, and the first and second continuous filaments may be at least partly fixed to the substrate sheet. Alternatively, the first and second continuous filaments may be at least partly fixed to each other.

The surface member of the present invention can be readily manufactured by fixing the first and second continuous filaments into the form of sheet.

BRIEF DESCRIPTION OF THE DRAWINGS

The present invention will be understood more fully from the detailed description given hereinafter and from the accompanying drawings of the preferred embodiments of the present invention, which, however, should not be taken to be limitative to the invention, but are for explanation and understanding only.

In the drawings.

DESCRIPTION OF THE PREFERRED EMBODIMENT

The present invention will be discussed hereinafter in detail in terms of the preferred embodiments of an absorbent article according to the present invention with reference to the accompanying drawings. In the following description, numerous specific details are set forth in order to provide a thorough understanding of the present invention. It will be obvious, however, to those skilled in the art that the present invention may be practiced without these specific details. In other instance, well-known structures are not shown in detail in order to avoid unnecessary obscurity of the present invention.

Figure 1:
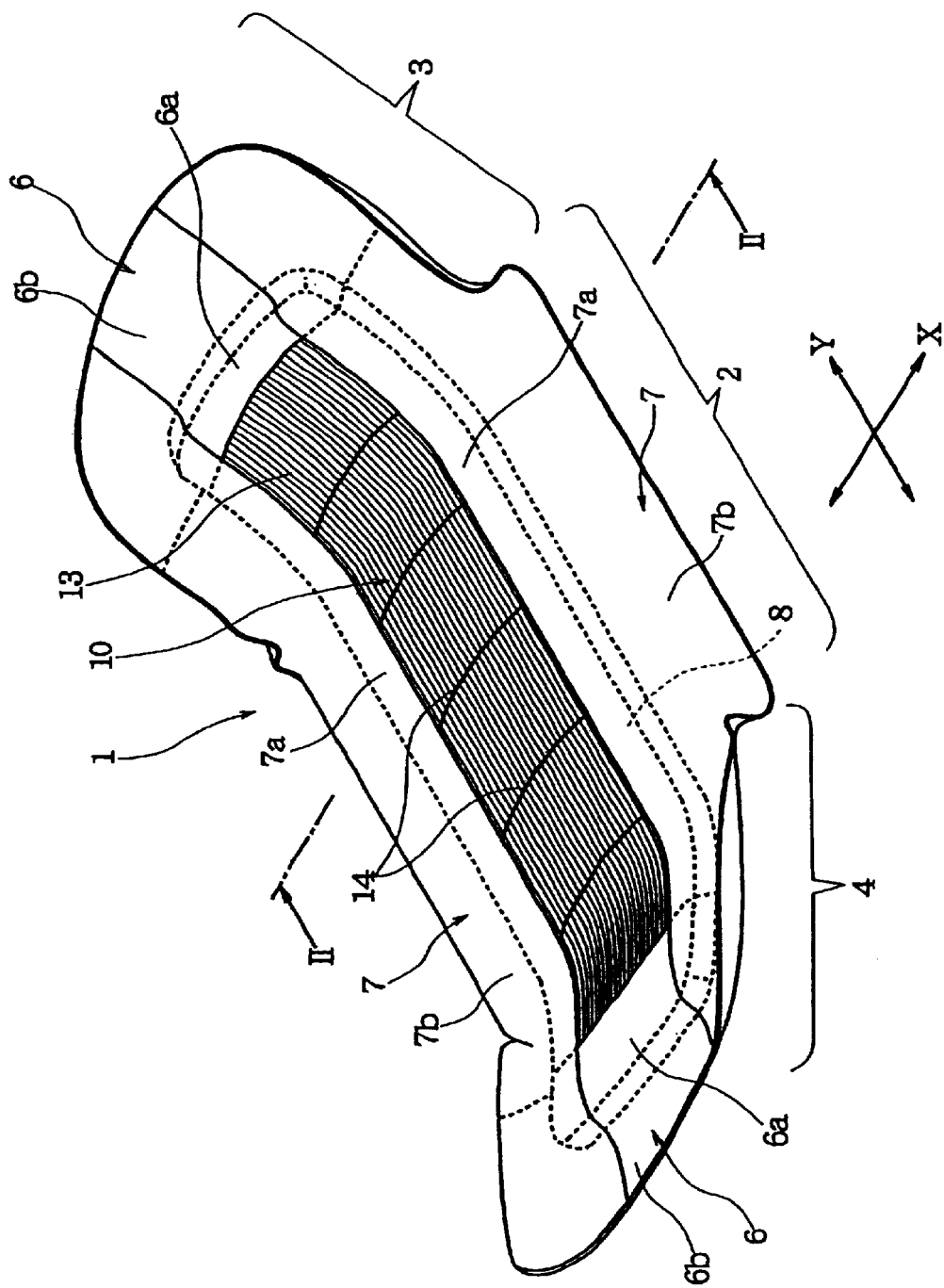
FIG. 1 is a perspective view showing an absorbent article according to a first embodiment of the invention.
Figure 2:
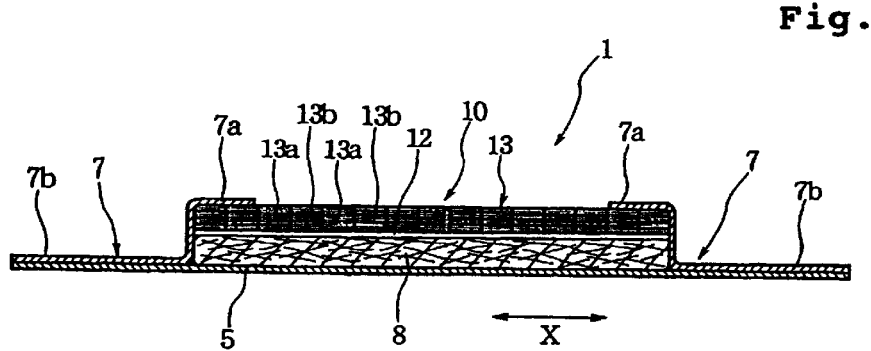
FIG. 2 is a cross-sectional view taken along line II—II of FIG. 1.
Figure 3:
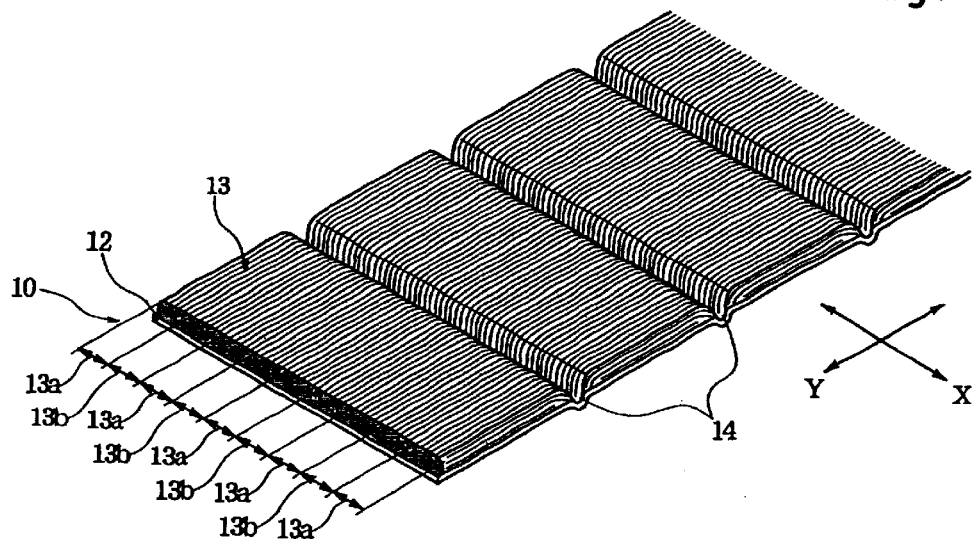
FIG. 3 is a perspective view showing a surface member employed for the absorbent article of FIG. 1.

FIG. 1 is a perspective view showing an absorbent article 1 according to a first embodiment of the invention; FIG. 2 is a cross-sectional view taken along line II—II of FIG. 1; and FIG. 3 is a perspective view showing a surface member employed for the absorbent article 1 according to the first embodiment.

The absorbent article 1 shown in FIG. 1 is a sanitary napkin, in which X-direction indicates a width direction (lateral direction) of the article 1, and Y-direction indicates a longitudinal direction of the article 1. The absorbent article 1 has an intermediate portion 2 between a front portion 3 and a rear portion 4.

As shown in the cross-sectional view of FIG. 2, the absorbent article 1 is constructed to mainly include: a liquid-impermeable backsheet 5; an absorbent core (absorbent layer) 8 laid on the backsheet 5; and a liquid-permeable and moisture-absorbent surface member 10 laid on the absorbent core 8. Detail of such construction employing the surface member has been disclosed in commonly owned co-pending U.S. patent application Ser. No. 09/934, 957. Disclosure of the above-identified commonly owned co-pending U.S. application is herein incorporated by reference. The absorbent article 1 is also provided with liquid-impermeable side sheets 7 covering the left and right side portions thereof and liquid-impermeable end sheets 6 covering the front and rear end portions thereof. The side sheets 7 are bonded at the portions 7a to the surface of the left and right side portions of the surface member 10; and are bonded at the remaining portions 7b to the surface of the backsheet 5, in both left and right flap portions. On the other hand, the end sheets 6 are bonded at the portions 6a to the surface of the surface member 10; and are bonded at the remaining portions 6b to the surface of the backsheet 5, in both front and rear flap portions.

The absorbent core 8 is disposed to extend over the intermediate portion 2 and parts of the front and rear portions 3 and 4 of the absorbent article 1. In the peripheral portion outside the absorbent core 8, the backsheet 5 is bonded with a hot melt adhesive or fusion-bonded with heat embossing to the portions 7b of the side sheets 7 and the portions 6b of the end sheets 6.

The liquid-impermeable backsheet 5 is formed from a moisture-permeable resin film, a nonwoven fabric or a laminate of a resin film and a nonwoven fabric. The absorbent core 8 is formed from a mixture of crushed pulp and SAP (superabsorbent polymer) wrapped in liquid permeable paper, air laid pulp formed into a sheet form by binder process, absorbent paper, a nonwoven fabric comprising mainly hydrophilic fibers, or the like.

The side sheets 7 and the end sheets 6 are formed from a nonwoven fabric, such as through-air bonded nonwoven fabric, point bonded nonwoven fabric, spunbonded nonwoven fabric, spunlaced nonwoven fabric, meltblown nonwoven fabric or air-laid nonwoven fabric, and are preferably hydrophobic or water-repellent.

As shown in FIGS. 2 and 3, the surface member 10 comprises a continuous filament layer 13 and a liquid-permeable substrate sheet underlying the continuous filament layer 13.

For example, the substrate sheet 12 is formed from a resin film of the polyolefin family, which is formed with apertures or cuts for passage of liquid. Alternatively, the substrate sheet 12 may be formed from a nonwoven fabric made of hydrophilic fibers only or made of hydrophilic fibers in combination with hydrophobic fibers. Preferably, the nonwoven fabric is formed with a large number of apertures.

The continuous filament layer 13 comprises first portions 13a and second portions 13b, which are combined to alternate with each other in the width direction (X-direction) of the absorbent article 1. Each first portion 13a has a predetermined width and is formed from first continuous filaments which are made of hydrophobic synthetic resin and individually extend over the entire length of the layer 13 without interruption. Likewise, each second portion 13b has a predetermined width but is formed from second continuous filaments which are made of cellulose acetate and individually extend over the entire length of the layer 13 without interruption. Weight ratio of the first continuous filaments forming the first portions 13a to the second continuous filaments forming the second portions 13b may be appropriately selected in a range of from 1:9 to 9:1.

The first and second continuous filaments are first prepared in the form of tow, respectively, in which continuous filaments are bundled in a crimped condition. Then, the tow of first continuous filaments and the tow of second continuous filaments are opened to form the first portions 13a and the second portions 13b, respectively.

The first continuous filaments forming the first portions 13a are made of heat-fusible hydrophobic synthetic resin. Examples of the first continuous filament include: monocomponent fibers such as those of PE (polyethylene), PP (polypropylene) or PET (polyethylene terephthalate); sheath/core structure bicomponent fibers such as those of PE/PET or PE/PP; and side-by-side structure bicomponent fibers such as those of PE/PET or PE/PP. The first continuous filaments are treated to be hydrophilic for use by applying a hydrophilic agent to their surfaces. Alternatively, the first continuous filaments may be made hydrophilic by blending a hydrophilic agent with the resin.

On the other hand, the second continuous filaments forming the second portions 13b are regenerated cellulose fibers made of cellulose acetate such as di- or tricellulose acetate. The second continuous filaments are prepared by extruding heated spinning solution through a series of small diameter nozzles into a hot air.

Both the first and second continuous filaments may contain 0.5 to 10% by weight of inorganic filler such as titanium oxide. With the inorganic filler, the filaments are made opaque so that menstrual blood absorbed by the absorbent core 8 can be easily concealed from external view. The first and second continuous filaments may be of a circular or modified cross-section.

The first and second continuous filaments after opened from the tows are both in a crimped condition. Crimp is provided upon production of the continuous filaments by means of crimper, and crimp frequency (i.e., number of crimp) is increased by pre-heating calender or hot air treatment. In an alternative, through pre-heating calender, drawing and relaxing are repeated to cause strain in orientation of resin forming continuous filaments to cause crimp in coil form.

Opening of a tow (or bundle) of crimped continuous filaments can be performed as follows. While the tow is transported between transporting rolls, tension force is applied in the direction along which the filaments extend, and then the tension force is released. These processes are repeated to separate individual continuous filaments from each other for opening. In an alternative, it is also possible to perform opening of the tow by urging sliding plates onto the tow from opposite sides. In this method, the tow transported between transporting rolls is slidingly contacted with the sliding plates, and individual filaments are separated from each other by sliding contact force for opening. The latter method employing the sliding plates has been disclosed in commonly owned co-pending U.S. patent application Ser. No. 09/935,407. The disclosure of the above-identified commonly owned co-pending U.S. Patent Application is herein incorporated by reference. The opened tow has a smaller filament density and a larger apparent width.

By the opening process, the first continuous filaments and the second continuous filaments are debundlized (or separated) from each other, respectively, so that the tows are spread (widened) in the width direction thereof to have a uniform bulkiness. Thereafter, each tow is separated into a plurality of narrow portions having a predetermined width. That is, the tow of first continuous filaments is separated into the first portions 13a; and the tow of second continuous filaments is separated into the second portions 13b. The first portions 13a and the second portions 13b are then fed onto the substrate sheet 12 while being combined to alternate with each other in the width direction of the absorbent article 1. The continuous filaments of the first and second portions 13a and 13b are fixed (or joined) to the substrate sheet 12 on a plurality of fixing lines 14 spaced apart in the longitudinal direction of the absorbent article 1, thereby forming the surface member 10 in the form of sheet.

The continuous filament layer 13 consisting of the first portions 13a and the second portions 13b has a basis weight of 10 to 100 g/m$^2$.

Fixing of the first and second continuous filaments to the substrate sheet 12 on the fixing lines 14 is performed such that a hot melt type adhesive is applied to the substrate sheet 12 in a striped pattern and then individual continuous filaments are pressed against the substrate sheet 12. The continuous filaments may also be fixed to the substrate sheet 12 with use of a hardening agent such as triacetin (glycerol acetate).

Here, it is also possible that the surface member 10 consists essentially of the first and second continuous filaments, without providing the substrate sheet 12. In this case, the individual continuous filaments forming the continuous filament layer 13 are fixed to each other on fixing lines into the form of a sheet.

In the absorbent article 1, when a large amount of liquid such as menstrual blood is given to the surface member 10, most of the liquid passes through the first portions 13a of the first continuous filaments, which are made of hydrophobic synthetic resin and treated to be hydrophilic, and then, passes through the substrate sheet 12 to be absorbed by the absorbent core 8 due to capillary action of the absorbent core 8. Part of the liquid, on the other hand, passes through the second portions 13b of the second continuous filaments, which are made of cellulose acetate, to be absorbed by the absorbent core 8.

On the other hand, a small amount of residual liquid on the surface of the first portions 13a, sweat, or vapor vaporized from the sweat is adsorbed in the second portions 13b due to moisture-absorbency of cellulose acetate.

In case where hydrophilicity of the cellulose acetate is set higher than that of the hydrophobic synthetic resin treated to be hydrophilic, a small amount of residual liquid, sweat or the like is effectively absorbed by the cellulose acetate. Here, when a large amount of liquid is given to the first continuous filaments of the hydrophobic synthetic resin, a hydrophilic agent applied to the surface of the first continuous filaments flows out to lower the hydrophilicity of the first continuous filaments. However, even when such a large amount of liquid passes through the layer 13, the hydrophilicity of the cellulose acetate is not lowered. Therefore, a small amount of residual liquid, sweat or the like adhered to the first continuous filaments having its hydrophilicity lowered, can be effectively adsorbed on the cellulose acetate.

Accordingly, the surface of the surface member 10 is always kept dry. In addition, the surface member 10 has excellent cushioning properties because its surface is formed from the continuous filament layer 13, providing softness when in contact with the wearer's skin. Therefore, the absorbent article hardly gives stuffy and wet feel to the wearer, thereby preventing skin roughness.

Figure 4:
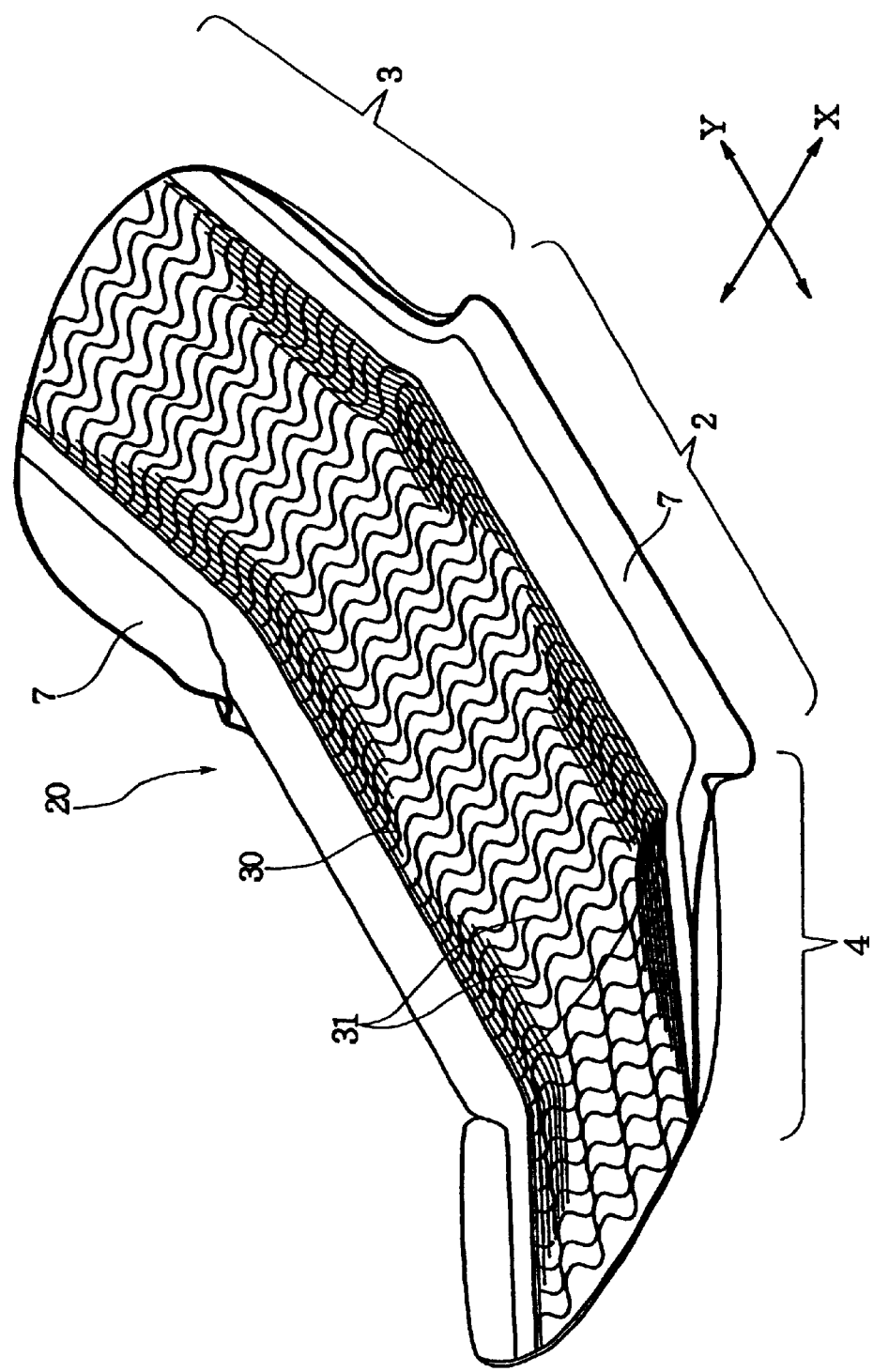
FIG. 4 is a perspective view showing an absorbent article according to a second embodiment of the invention.
Figure 5:
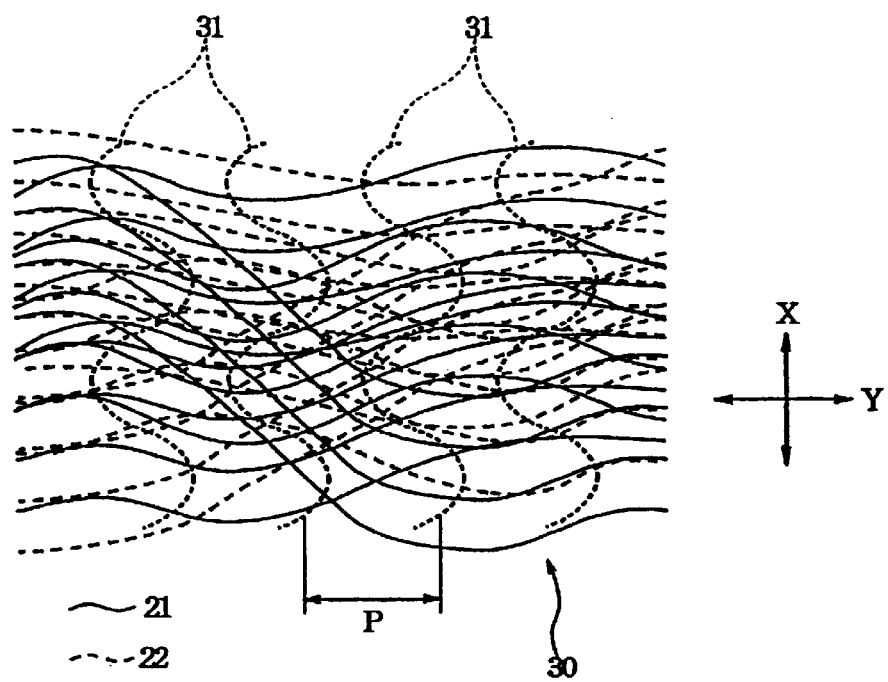
FIG. 5 is a plan view schematically showing a portion of a surface member employed for the absorbent article of FIG. 4.
Figure 6:
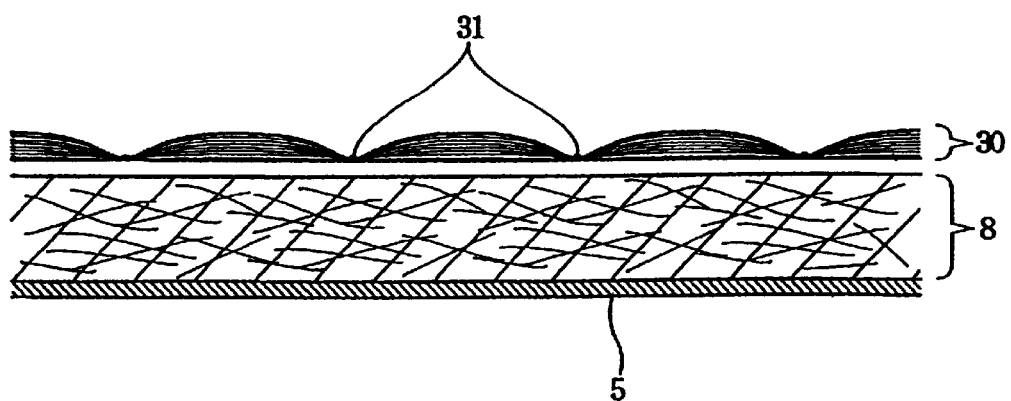
FIG. 6 is a cross-sectional view of a portion of the absorbent article of FIG. 4.

FIG. 4 is a perspective view showing an absorbent article (sanitary napkin) 20 according to a second embodiment of the invention, FIG. 5 is a plan view schematically showing a portion of a surface member employed for the absorbent article 20, and FIG. 6 is a cross-sectional view of a portion of the absorbent article 20.

The absorbent article 20 shown in FIGS. 4 to 6 has a surface member 30 extending over the entire length of the article 20, i.e., from the front portion 3, through the intermediate portion 2 to the rear portion 4. The side sheets 7 are bonded to both side portions of the surface member 30, respectively. The absorbent core 8 is interposed between the surface member 30 and the backsheet 5.

The surface member 30 is a layer of continuous filaments individually extending over the entire length of the surface member 30 without interruption. The continuous filaments comprise the first continuous filaments of hydrophobic synthetic resin treated to be hydrophilic and the second continuous filaments of cellulose acetate. In this surface member 30, however, the first and second continuous filaments are uniformly mixed, unlike those in the surface member 10 of the first embodiment. The first and second continuous filaments thus mixed are partly fixed to each other with use of a hot melt adhesive or triacetin. In case where the first continuous filaments of hydrophobic synthetic resin are heat-fusible, the first and second continuous filaments may be fixed to each other by thermally bonding the first continuous filaments to each other so that second continuous filaments of cellulose acetate are held between adjacent first continuous filaments thus thermally bonded.

The sheet formed only from the first and second continuous filaments has a basis weight of 10 to 100 g/m$^2$. It is, of course, possible to stack the mixed first and second continuous filaments on a substrate sheet and partly fix the filaments to the substrate sheet into the form of sheet, as in the first embodiment shown in FIGS. 1 to 3.

In FIG. 5, the first continuous filaments are indicated at 21; the second continuous filaments are indicated at 22. On the other hand, the fixing lines on which the first and second continuous filaments are fixed to each other are indicated at 31. As shown in FIGS. 4 and 5, the individual fixing lines 31 extend across the surface member 30 in the X-direction in the form of continuous line approximated to trigonometric curve. The fixing lines 31 are spaced apart from each other in the Y-direction.

As has been described hereinabove, the first continuous filaments 21 and the second continuous filaments 22 are initially prepared in the form of tow, respectively. The first continuous filaments 21 and the second continuous filaments 22 can be uniformly dispersed in the surface member 30 such that the opened tow of first continuous filaments 21 and the opened tow of second continuous filaments 22 are stacked or preliminarily mixed and are then given a dispersing or mixing force in accordance with hydroentangling method. When the first and second continuous filaments 21 and 22 are dispersed and mixed with water jets, a hydrophilic agent having been applied to the first continuous filaments 21 of hydrophobic synthetic resin flows out to lower the hydrophilicity thereof. Even in this case, however, the hydrophilicity of the second continuous filaments 22 of cellulose acetate is never lowered. Therefore, the surface member 30 has an appropriate hydrophilicity as a whole.

In this embodiment, too, weight ratio of the first continuous filaments 21 to the second continuous filaments 22 may be appropriately selected in a range of from 9:1 to 1:9.

In the absorbent article 20, a large amount of liquid given to the surface member 30 readily passes through it due to the presence of the first continuous filaments 21 of hydrophobic synthetic resin, and is then drawn and absorbed by the underlying absorbent core 8 due to capillary action thereof. On the other hand, a small amount of liquid on the surface of the surface member 30 or vapor can be adsorbed due to water- and moisture-absorbency of cellulose acetate, thereby preventing the surface of the surface member 30 from staying in a wet condition.

In the foregoing embodiments the absorbent article of the invention is exemplified in the form of sanitary napkin, but is also applicable for disposable diapers, incontinence pads, panti-liners or the like.

As has been described hereinabove, since the surface member of the present invention comprises the first continuous filaments of hydrophobic synthetic resin and the second continuous filaments of cellulose acetate, the surface member provides good liquid-permeability and moisture-absorbency, thereby preventing stuffy and wet feel on the surface thereof.

Although the present invention has been illustrated and described with respect to exemplary embodiments thereof, it should be understood by those skilled in the art that the foregoing and various other changes, omission and additions may be made therein and thereto, without departing from the spirit and scope of the present invention. Therefore, the present invention should not be understood as limited to the specific embodiments set out above but to include all possible embodiments which can be embodied within a scope encompassed and equivalent thereof with respect to the feature set out in the appended claims.

What is claimed is:

1. An absorbent article comprising:
   a liquid-permeable surface member;
   a backsheet; and
   an absorbent core positioned between said surface member and said backsheet, said surface member being a sheet comprising: first continuous filaments made of hydrophobic synthetic resin and individually extending over an entire length of said surface member; and second continuous filaments made of cellulose acetate and individually extending over the entire length of said surface member;
   wherein said first continuous filaments are treated to be hydrophilic, and a hydrophilicity of said second continuous filaments is higher than the hydrophilicity of said first continuous filaments.

2. The absorbent article as set forth in claim 1, wherein said first continuous filaments and said second continuous filaments are mixed with each other in said surface member.

3. The absorbent article as set forth in claim 1, wherein said surface member further comprises a liquid-permeable substrate sheet underlying said first and second continuous filaments, and said first and second continuous filaments are at least partly fixed to said substrate sheet.

4. The absorbent article as set forth in claim 1, wherein said first and second continuous filaments are at least partly fixed to each other.

5. An absorbent article comprising:
   a liquid-permeable surface member;
   a backsheet; and
   an absorbent core positioned between said surface member and said backsheet, said surface member being a sheet comprising: first continuous filaments made of hydrophobic synthetic resin which individually extend over an entire length of said surface member and form first portions; and second continuous filaments made of cellulose acetate which individually extend over the entire length of said surface member and form second portions;
   wherein said first portions alternate with said second portions.

6. The absorbent article as set forth in claim 5, wherein said surface member further comprises a liquid-permeable substrate sheet underlying said first and second continuous filaments, and said first and second continuous filaments are at least partly fixed to said substrate sheet.

7. The absorbent article as set forth in claim 5, wherein said first and second continuous filaments are at least partly fixed to each other.

* * * * *